United States Patent [19]
Andresen et al.

[11] Patent Number: 5,525,799
[45] Date of Patent: Jun. 11, 1996

[54] PORTABLE GAS CHROMATOGRAPH-MASS SPECTROMETER

[75] Inventors: Brian D. Andresen; Joel D. Eckels, both of Livermore; James F. Kimmons, Manteca; David W. Myers, Livermore, all of Calif.

[73] Assignee: The United States of America as represented by the United States Department of Energy, Washington, D.C.

[21] Appl. No.: 225,111

[22] Filed: Apr. 8, 1994

[51] Int. Cl.$^6$ .............................. G01D 59/44; H01J 49/00
[52] U.S. Cl. ........................................ 250/288; 250/281
[58] Field of Search .................................. 250/281, 288, 250/288 A

[56] References Cited

U.S. PATENT DOCUMENTS

| | | | |
|---|---|---|---|
| 3,641,339 | 2/1972 | McCormick | 250/41.9 G |
| 4,442,353 | 4/1984 | Baubron | 251/288 |
| 4,888,295 | 12/1989 | Zaromb et al. | 436/161 |
| 5,142,144 | 8/1992 | Remo et al. | 250/288 |
| 5,153,433 | 10/1992 | Andresen et al. | 250/296 |
| 5,313,061 | 5/1994 | Drew et al. | 250/281 |
| 5,401,963 | 3/1995 | Sittler | 250/288 |

*Primary Examiner*—Bruce C. Anderson
*Attorney, Agent, or Firm*—L. E. Carnahan; William C. Daubenspeck; William R. Moser

[57] ABSTRACT

A gas chromatograph-mass spectrometer (GC-MS) for use as a field portable organic chemical analysis instrument. The GC-MS is designed to be contained in a standard size suitcase, weighs less than 70 pounds, and requires less than 600 watts of electrical power at peak power (all systems on). The GC-MS includes: a conduction heated, forced air cooled small bore capillary gas chromatograph, a small injector assembly, a self-contained ion/sorption pump vacuum system, a hydrogen supply, a dual computer system used to control the hardware and acquire spectrum data, and operational software used to control the pumping system and the gas chromatograph. This instrument incorporates a modified commercial quadrupole mass spectrometer to achieve the instrument sensitivity and mass resolution characteristic of laboratory bench top units.

20 Claims, 3 Drawing Sheets

PORTABLE GAS CHROMATOGRAPH-MASS SPECTROMETER

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to chemical analysis instruments, particularly to gas chromatograph-mass spectrometers (GC-MS), and more particularly to a small portable high resolution GC-MS which can be used as a field portable organic chemical analysis instrument with the sensitivity and specificity of a highly sophisticated laboratory GC-MS.

Instruments which identify unknown chemical compounds using gas chromatography-mass spectrometry (GC-MS) are well known, as exemplified by U.S. Pat. No. 3,641,339 issue Feb. 8, 1972 to A. McCormick. However, such instruments are generally located in laboratories or other research facilities for example, and thus, unknown chemicals must be transported to such facilities for analysis. Such takes considerable time and expense compared to chemical analysis in the field or location of the unknown chemical. However, until recently, portable GC-MS systems were not available. Recent efforts to develop portable chemical analysis systems are exemplified by U.S. Pat. No. 4,888,295 issued Dec. 19, 1989 to S. Zaromb et al. and No. 5,153,433 issued Oct. 6, 1992 to B. D. Andresen et al.

Portable or field deployable GC-MS systems, such as the Viking Spectra Trak, made by Viking Instruments, Reston, Va., are expensive, costing over $150,000 and weigh approximately 150 pounds, and utilize an existing commercial mass spectrometer vacuum system which requires dolly transport. Thus, the prior known portable systems are both expensive and difficult to take to the field because of size and weight thereof. In addition, the power consumption of the prior known portable systems, such as the above-referenced Viking Spectra Trak, is between 1,000 to 1,500 watts depending upon the operational mode.

The recent environment concerns and market has generated opportunities to widely utilize field deployable GC-MS systems. The critical need for a small portable chemical analysis instrument, which is easy to use in a field environment, but which provides laboratory-grade data, has generated much interest among potential users. The need for such instruments is worldwide in scope. The need is driven by the increasing public awareness of environmental issues, and secured by extensive and growing public policy and regulations impacting those issues. The following outlines various current and new future applications for high resolution portable GC-MS instruments:

1. Forensics: The support of law enforcement for the analysis of drugs, crime scene evidence, accident debris, and arson residues.
2. Chemical Weapons and Treaty Monitoring; To assure compliance and the nonproliferation of chemical weapons, which require sensitive and specific analyses.
3. Regional Transit Authorities: For fast response analysis of spills and accidents on the roadways.
4. Environmental Laboratories: To provide an instrument which can be operated in the laboratory or quickly taken out into the field for special analysis projects.
5. Medical and Hospital: Various diagnostic analysis of patients relative to drug overdose, poisoning, and illness which can be carried in ambulance and/or emergency rooms.
6. Universities: Chemical analysis class work and research.
7. Industries: Monitoring chemical wastes, production chemicals, assembly line quality control, and other manufacturing processes.
8. Commercial and Military Airport Security: Looking for bombs (explosive vapors) and drugs (residues) in luggage or packages, and in cargo containers, etc.

Thus, there is need for a readily portable, high resolution, gas chromatograph-mass spectrometer. The exact chemical characterization of unknown substances in the environment, at crime scenes, at accident sites, or in an emergency room to aid the analysis of a poisonous substance is often very important. The removal of samples and transport of the material to a housed laboratory setting is both costly and time consuming. This need has been satisfied by the present invention which involves a small, portable, lightweight (less than 70 pounds), low power consumption (under 600 watts at peak power), GC-MS system which can be incorporated in a 9.5×18×27 inch suitcase, and thus enables immediate chemical analyses in the field. Samples are simply analyzed and the results seen on a large liquid crystal screen.

SUMMARY OF THE INVENTION

It is an object of the present invention to provide a portable gas chromatograph-mass spectrometer.

A further object of the invention is to provide a lightweight, low power consumption, instrument for identifying unknown chemical compounds.

Another object of the invention is to provide a compact gas chromatograph-mass spectrometer contained within a conventional sized suitcase.

Another object of the invention is to provide a portable, high resolution gas chromatograph-mass spectrometer which includes a conduction heated, forced air cooled small bore capillary gas chromatograph, a self contained ion/sorption pump vacuum system, hydrogen supply, and a dual computer system used to control the hardware and acquire spectrum data.

Another object of the invention is to provide a suitcase size, portable, high resolution gas chromatograph-mass spectrometer weighing less than seventy pounds and requiring less than 600 watts of electric power at peak power.

Other objects and advantages will become apparent from the following description and accompanying drawings. Basically, the invention is a field portable organic chemical analysis instrument. More specifically, the invention is a gas chromatograph-mass spectrometer (GC-MS) which has the sensitivity and mass resolution characteristics of laboratory bench top units, but is portable and has low electrical energy consumption. The instrument of this invention weights less than 70 pounds and uses less than 600 watts of electrical power at peak power (all systems on). More specifically, the GC-MS of this invention includes: a conduction heated, forced air cooled small bore capillary gas chromatograph, an injector assembly, a self contained ion/sorption pump vacuum system, a self-contained hydrogen supply, a dual computer system uses to control the hardware and acquire spectrum data, and operation software used to control the pumping system and the gas chromatograph. The instrument incorporates a modified commercial quadrupole mass spectrometer to achieve the instrument sensitivity and mass resolution, which is comparable to larger laboratory instruments.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

Figure 1:
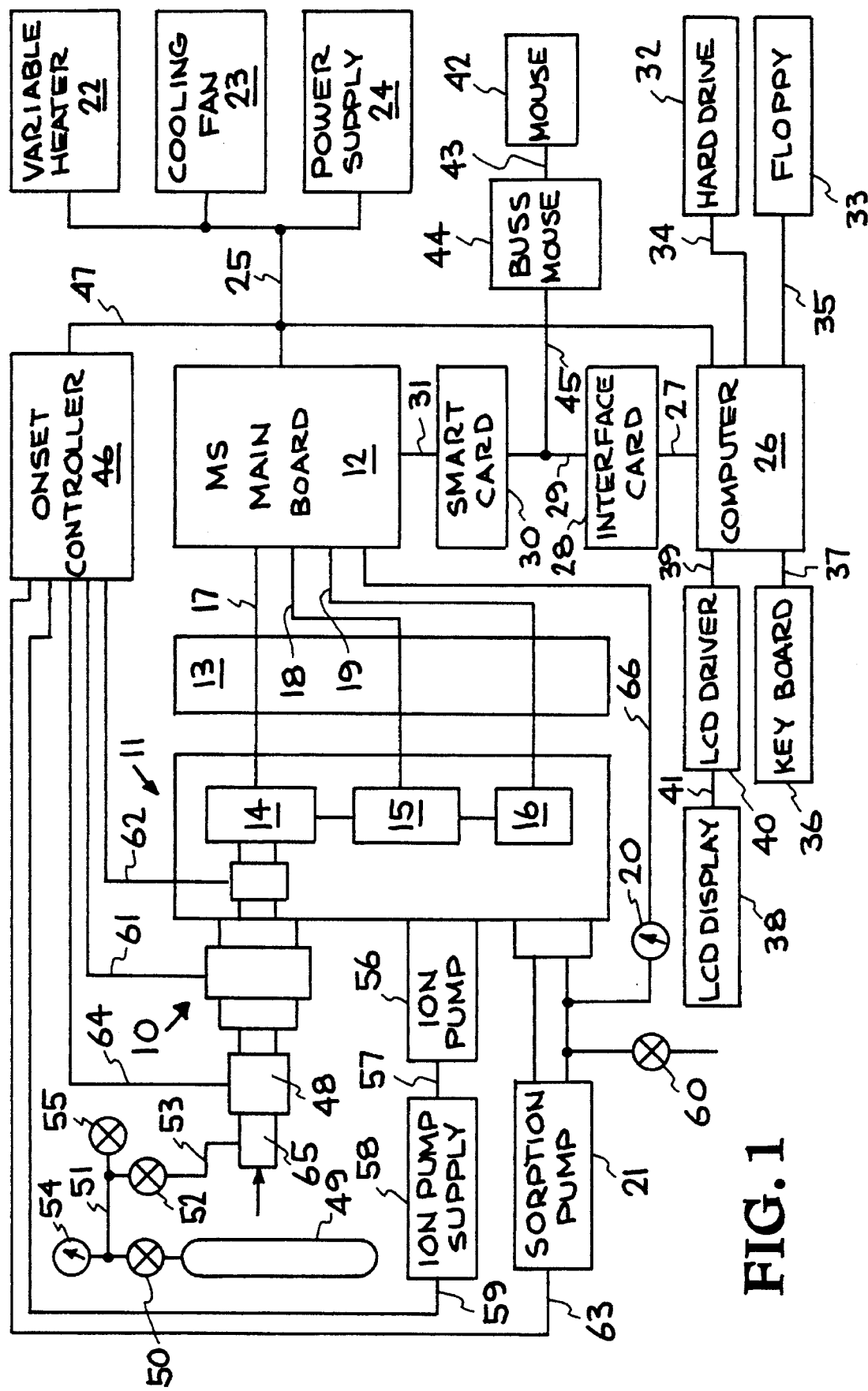
FIG. 1 illustrates the various components of an embodiment of the invention, and the operational interconnection between the components.

The present invention involves an instrument which identifies unknown chemical compounds using gas chromatography and mass spectrometry (GC-MS). More specifically, the invention is directed to a portable, high resolution GC-MS which is completely contained in a 9.5×18×27 inch suitcase, and which weighs less than 70 pounds and requires less than 600 watts of electrical power with all systems on (peak power), with typical power drain of 150–200 watts. The embodiment illustrated and described hereinafter weighs 60 pounds and has a peak power consumption of 300 watts. Hydrogen, as the carrier gas for example, is used in a small gas chromatograph that separates compounds in a complex mixture prior to their introduction into an ion source of an electron impact mass spectrometer. The instrument is designed with dual microprocessor controllers. One system runs a gas chromatograph, placed in an ultra small oven attached to an inlet port of a quadrupole mass spectrometer. Dual computer systems control the heating of the gas chromatograph while the other microprocessor operates the mass spectrometry functions, data storage, display and archiving of the data. Aside from the important aspect of portability, the instrument of the present invention brings to the analytical community:

1. A light weight vacuum-sorption pumping system which uses pelletized stable-state zirconium getter metal to sequester the hydrogen GC-carrier gas in combination with an ion getter pump to remove any extraneous gases.
2. A vacuum chamber and high vacuum pumping system having no moving parts and operated without sound.
3. A flat-packed gas chromatograph and capillary column for ultimate gas chromatographic separation of organic compounds, with hydrogen utilized for the carrier gas, which allows the zirconium pump to operate efficiently.
4. Software to control all aspects of the GC instrument operations and the vacuum pumps.
5. A modified vacuum housing and parts design for optimization of parts placement and overall reduction of size of the suitcase GC-MS instrument.
6. Field calibration and tuning of the mass spectrometer.
7. Optimum mass resolution for a fieldable apparatus, with the unit mass range of the instrument being maintained to 650 mass units.

In addition to portability (size and weight) and low power consumption, the GC-MS instrument of this invention includes a self-contained ion/sorption pump vacuum system, requiring only one-fourth of the total suitcase space, and which was designed to permit maximum field use and high vacuum environments without the need of bulky and heavy mechanical pumps. The GC-MS incorporates an ion pump to remove trace gas impurities and a 250 L/sec. sorption pumping system to remove hydrogen. The portable instrument design also permits conventional replacement of the sorption pump in the field, without raising the entire system to air.

As pointed out above, and by way of comparison, the Viking Spectra Trak, field deployable GC-MS system weighs about 150 pounds and has a power consumption of 1000–1500 watts, compared to the weight of less than 70 pounds and peak power consumption of less than 600 watts of the portable GS-MS system of this invention. The GC-MS instrument of the present invention allows chemical analysis in the field with the sensitivity and specificity of a highly sophisticated laboratory GC-MS. The forensic platform allows immediate field characterization of organic compounds. Through the application of advanced electronics, ultrasmall gas chromatographic techniques, and new vacuum pumping systems which work in concert, the instrument is capable of highly refined chemical analyses for environmental monitoring of pollution, emergency response of chemical spills and industrial accidents, law enforcement, and international chemical weapons treaty negotiations, in a timely manner in the field.

The following Table illustrates a system specification for a portable GCMS made in accordance with the present invention:

| SYSTEM SPECIFICATIONS | |
| --- | --- |
| Goal | Status |
| Mass Range | |
| 45–650 amu | 10–650 amu |
| Resolution m/Δm > 1000 | 0.5 amu (MS limit) |
| Size, Weight | |
| Small | 9.5 × 18 × 27 inches |
| Transportable | 60 lbs. |
| Power Consumption | 300 Watts Pk. (117 Vac) |
| Low Power | |
| GC Temperatures | |
| RT to 300° C. | RT to 280° C. |
| Linear 10° / min. | Programmable |
| Software controlled | |
| Carrier Gas | |
| Hydrogen | Yes |
| ≦1 mL per minute | 0.08 mL per minute |
| >20 runs before replacement | greater than 500 injections |
| Vacuum Requirements | 2 mon. eval. verification |
| $5 \times 10^{-5}$ Torr | |
| Data Collection System | |
| Range $10^5$ | HP specs. using the 5971 |
| Resolution 16 bits | Quadrupole |
| Scan Speed – 1 Second | |
| Operator Interface | |
| Display | Graphics LC (color) |

| SYSTEM SPECIFICATIONS | |
|---|---|
| Goal | Status |
| Multiple Input Devices | Keyboard/Mouse |

Referring now to the drawings, FIG. 1 illustrates by block diagram the various components of the portable GC-MS instrument and the operational interconnection of these components, with the various power and control wires, lines, or leads being indicated generally for clarity purposes. The gas chromatograph (GC) column is generally indicated at 10 and the mass spectrometer (MS) is generally indicated at 11, with a main control board 12 being connected through a power control panel 13 to an ion source 14, quadrupole 15, and detector 16 via the leads or lines 17, 18 and 19 respectively. Also, control board 12 is connected to a convection gauge 20 of sorption pump 21 as indicated via a line or lead 66. The MS main control board 12 is additionally connected to a variable heater 22, a cooling fan 23, and a power supply 24, as indicated via line 25 for controlling units 22–24.

A computer 26 is connected to the main control board 12 as indicated via line 27, interface card arrangement 28, line 29, smart card arrangement 30 and line 31. Smart card 30 comprises a conventional microcontroller CPU board with dedicated software and hardware to perform specific input/output (I/O) between the real world and a CPU. Such cards may be commercially purchased and programmed to the specific needs of the user. Computer 26 includes a hard drive 32 and a floppy disc drive 33, as indicated via leads 34 and 35, and is connected to a keyboard 36 via lead 37 and to a liquid crystal display (LCD) 38 via lead 39, an LCD driver 40, and lead 41. A mouse 42 is connected to the computer 26 as indicated via lead 43, a buss mouse 44, lead 45, and lead 29. Computer 26 is additionally connected to an onset controller 46 as indicated by lead 47, with onset controller 46 additionally being connected to heater 22, cooling fan 23 and power supply 24, as indicated via lines or leads 25 and 47.

The GS 10 includes an injector 48 to which a self-contained hydrogen (H$_2$) supply 49 is connected via valve 50, line 51, valve 52 and line 53. A gauge 54 and a bleed valve 55 are connected to line 51 intermediate valves 50 and 52. An ion pump 56 is connected to MS 11 and to onset controller 46 via line 57, ion pump supply 58 and line 59. Sorption pump 21 is provided with a bleed valve 60. Each of the GC 10, ion source 14, sorption pump 21, and injector 48 include a variable heating element, not shown, but connected to variable heater 22 via onset controller 46 and leads 61, 62, 63 and 64 respectively. Sample gas, etc. to be tested is directed into an inlet 65 of injector 48 as indicated by the inlet arrow.

Figure 2:
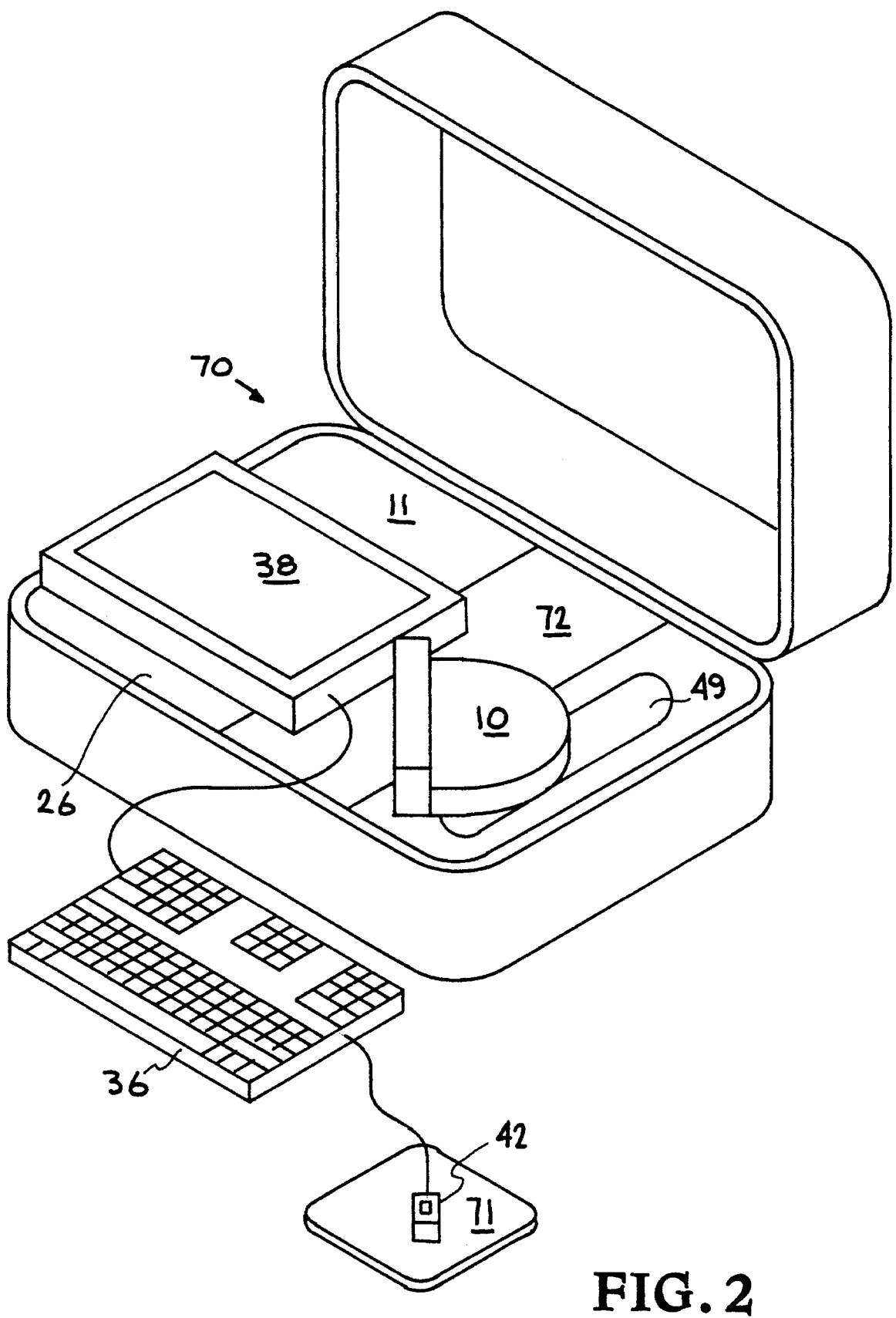
FIG. 2 illustrates an embodiment of a portable gas chromatograph-mass spectrometer (GC-MS), made in accordance with the invention, mounted in a standard suitcase having a movable separator therein.

FIG. 2 illustrates an embodiment of a conventional suitcase (27 inch length, 18 inch width, and 9.5 inch height) containing the components shown in FIG. 1, with the weight thereof being less than 70 pounds. As shown, the suitcase, generally indicated at 70 in which the MS 11, and associated components including control board 12, ion pump 56, and sorption pump 21, and the computer 26, and associated components, are located under the LCD display 38. The key board 36 and mouse 42, positioned on a pad 71, are located in their operational position exterior of the suitcase 70, but are stored within the suitcase. The GS 10, and associated components including injector 48, and hydrogen supply 49 are mounted in an upper section of the suitcase, with the various electrical, power control, etc. leads, wires, lines, being located beneath a movable separator plate or shelf 72 of the suitcase 70.

Figure 3:
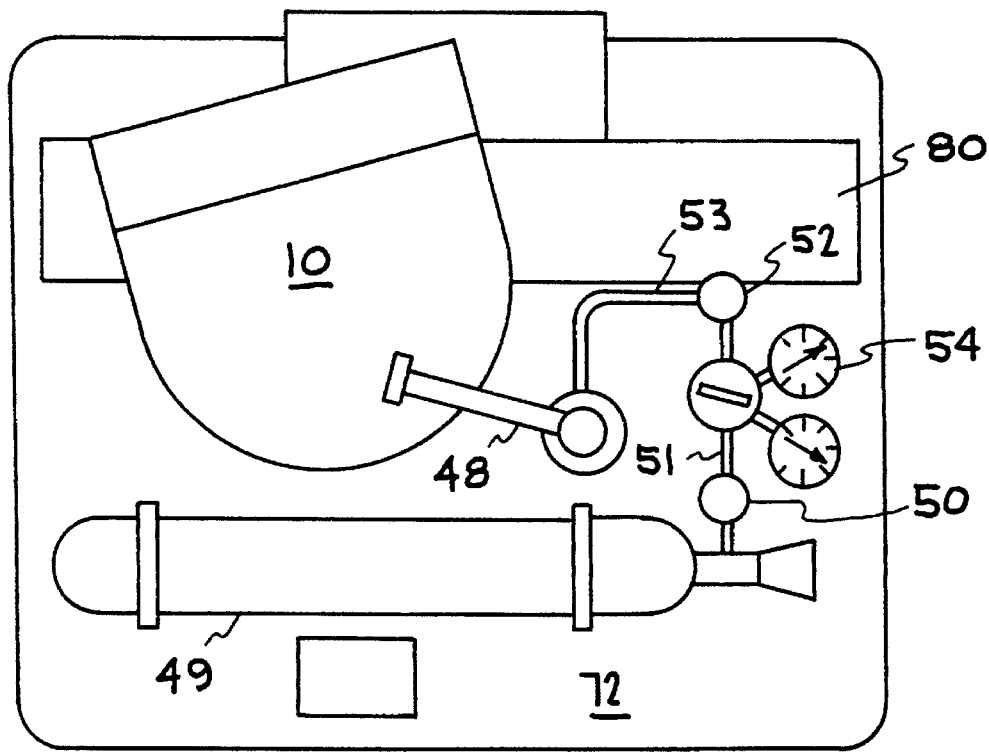
FIG. 3 is a plan view of the suitcase of FIG. 2 illustrating components of FIG. 1 located above the separator.
Figure 4:
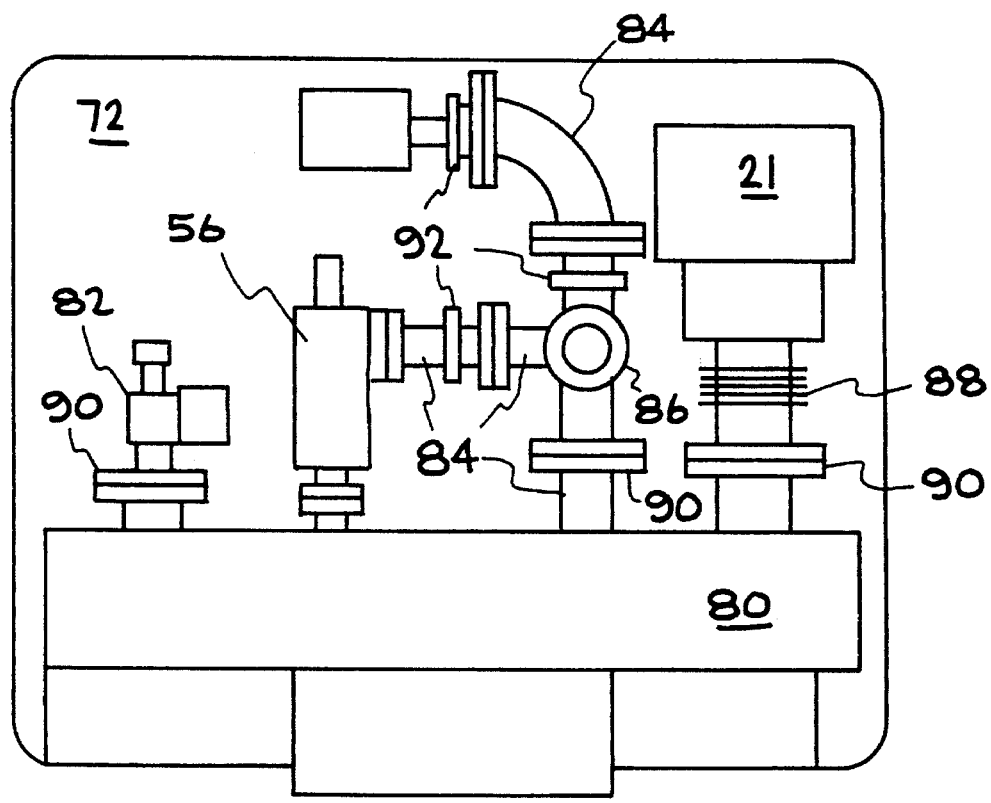
FIG. 4 is a plan view of the suitcase of FIG. 2 illustrating components of FIG. 1 located below the separator.

The separator plate 72 which extends partially across suitcase 70 may be hinged or otherwise moveably secured in suitcase 70 so as to provide a support or base for components positioned thereon, while providing access to components positioned thereunder, as shown in FIGS. 3 and 4. As seen in FIG. 3, components of FIG. 1 positioned above the separator plate 72 include the self-contained hydrogen (H$_2$) supply 49, valve 50, line 51, gauge 54, valve 52, injector 48, GC10, and vacuum housing 80. Components of FIG. 1 located beneath the separator plate 72 of suitcase 70 are illustrated in FIG. 4, and include the sorption pump 21, ion pump 56, vacuum housing 80, vacuum tubing 84, pump out port 86, bellows 88, flanges 90, and support brackets 92.

It is pointed out that the location, configuration, and interconnection of the components of FIG. 1, as shown in FIGS. 2, 3 and 4 are not critical to this invention, inasmuch as efforts are continuing to reconstruct and relocate the various components in the suitcase to reduce the size and weight of the overall system.

Inasmuch as the various components of the above described GC/MS system are known, a detailed description is deemed unnecessary to enable one skilled in this field to use the present invention. The FIG. 1 system has been experimentally verified with excellent results.

It has thus been shown that the present invention provides a compact, portable GC-MS system which can be used in both laboratory and field conditions. Also, this invention provides substantial capability with only a little power drain (typical power drain of 150–200 watts, with peak power drain of 600 watts). Thus, this invention enables the rapid analysis of unknown materials, thereby reducing the problems associated with the release or distribution of unknown substances, for example.

While a particular embodiment of the invention has been described and/or illustrated to explain the principles of this invention, such is not intended to limit the scope of the invention. Modifications and changes will become apparent to those skilled in the art, and it is intended that the invention be limited only by the scope of the appended claims.

We claim:

1. A compact, portable gas chromatograph-mass spectrometer adapted to be contained in a suitcase, including:

a mass spectrometer;

a gas chromatograph column;

a liquid crystal display;

a self-contained hydrogen supply; and a computer operatively connected to at least a liquid crystal display and said mass spectrometer;

said gas chromatograph-mass spectrometer having a weight of not greater than 70 pounds, a normal electrical power drain of about 150–200 watts, and an overall system peak electrical power drain of not greater than 600 watts.

2. The gas chromatograph-mass spectrometer of claim 1, wherein said mass spectrometer includes an ion source, a quadrupole, a detector, an ion pump, a sorption pump, and a control board operatively connected to said computer.

3. The gas chromatograph-mass spectrometer of claim 2, wherein said gas chromatograph column includes an injector operatively connected to said hydrogen supply.

4. The gas chromatograph-mass spectrometer of claim 3, additionally including an onset controller operatively connected to said computer and operatively connected to each of said ion source, gas chromatograph column, injector, ion pump and sorption pump.

5. The gas chromatograph-mass spectrometer of claim 4, wherein said control board of said mass spectrometer and said onset controller are each operatively connected to a power supply, a cooling fan, and a variable heater.

6. The gas chromatograph-mass spectrometer of claim 5, wherein said variable heater is operatively connected to each of said ion source, gas chromatograph column, injector and sorption pump.

7. The gas chromatograph-mass spectrometer of claim 6, wherein said computer includes a hard drive and floppy disc drive, and is operatively connected to a mouse and to a key board.

8. The gas chromatograph-mass spectrometer of claim 7, wherein said computer is operatively connected to said control board of said mass spectrometer via an interface card arrangement and a smart card arrangement.

9. The gas chromatograph-mass spectrometer of claim 8, wherein said gas chromatograph column is operatively corrected to said ion source of said mass spectrometer.

10. The gas chromatograph-mass spectrometer of claim 1, having a weight of about 60 pounds.

11. The gas chromatograph-mass spectrometer of claim 10, having a peak power drain of not greater than 300 watts.

12. A portable chemical analysis mechanism, comprising:
   a suitcase;
   a mass spectrometer mounted in said suitcase;
   a gas chromatograph column operatively connected to said mass spectrometer and mounted in said suitcase;
   a self-contained hydrogen supply operatively connected to said chromatograph column and mounted in said suitcase;
   a computer operatively connected to at least said mass-spectrometer and mounted in said suitcase;
   a liquid crystal display operatively connected to said computer and positioned in said suitcase; and
   power supply means for various components mounted in said suitcase;
   said chemical analysis mechanism having a normal electrical power drain of about 150–200 watts, an overall system peak power drain of about 300 watts, and having a weight of not greater than 60 pounds.

13. The mechanism of claim 12, additionally including variable heater means for said mass-spectrometer and said gas chromatograph column, and mounted in said suitcase.

14. The mechanism of claim 12, wherein said mass spectrometer includes an ion source, a quadrupole, a detector, an ion pump, a sorption pump, and a main control board operatively connected to said ion source, quadrupole, detector and sorption pump, said computer being operatively connected to said main control board.

15. The mechanism of claim 14, wherein said computer is operatively connected to said onset controller, said onset controller being operatively connected to said main control board, to a variable heater, a cooling fan, a power supply and to components of said gas chromatograph column and said mass spectrometer.

16. The mechanism of claim 12, wherein said gas chromatograph column includes an injector operatively connected to said hydrogen supply.

17. The mechanism of claim 12, additionally including a keyboard and a mouse, each being operatively connected to said computer and removably positioned in said suitcase.

18. The mechanism of claim 12, wherein said computer includes a hard drive and floppy disc drive.

19. The mechanism of claim 12, wherein said computer is operatively connected to a main control board for said mass spectrometer via an interface card arrangement and a smart card arrangement.

20. The mechanism of claim 12, wherein said suitcase has a length of about 27 inches, a width of about 18 inches, a height of about 9.5 inches.

* * * * *